(12) United States Patent
Wilson et al.

(10) Patent No.: US 11,974,868 B2
(45) Date of Patent: May 7, 2024

(54) SLED-TABLE FOR RADIOGRAPHIC IMAGING AND MEDICAL DEVICE INTEGRATION

(71) Applicant: Egg Medical, Inc., Arden Hills, MN (US)

(72) Inventors: Robert F. Wilson, Arden Hills, MN (US); John P. Gainor, Arden Hills, MN (US); James Montague, Arden Hills, MN (US); Uma S. Valeti, Arden Hills, MN (US)

(73) Assignee: Egg Medical, Inc., Arden Hills, MN (US)

( * ) Notice: Subject to any disclaimer, the term of this patent is extended or adjusted under 35 U.S.C. 154(b) by 0 days.

(21) Appl. No.: 17/815,442

(22) Filed: Jul. 27, 2022

(65) Prior Publication Data

US 2022/0354442 A1    Nov. 10, 2022

Related U.S. Application Data

(63) Continuation of application No. 16/578,128, filed on Sep. 20, 2019, now Pat. No. 11,432,780.
(Continued)

(51) Int. Cl.
*A61B 6/04* (2006.01)
*A61B 6/10* (2006.01)

(52) U.S. Cl.
CPC .............. *A61B 6/0407* (2013.01); *A61B 6/04* (2013.01); *A61B 6/0442* (2013.01); *A61B 6/107* (2013.01); *A61G 2203/80* (2013.01)

(58) Field of Classification Search
CPC ....... A61B 6/0407; A61B 6/04; A61B 6/0487; A61B 6/032; A61B 6/4441; A61B 5/055;
(Continued)

(56) References Cited

U.S. PATENT DOCUMENTS

| 4,652,758 A | 3/1987 | Barfod |
| 4,700,938 A | 10/1987 | Chambron |

(Continued)

FOREIGN PATENT DOCUMENTS

| DE | 102014216497 A1 | 11/2015 |
| EP | 3266377 A1 | 7/2017 |

(Continued)

OTHER PUBLICATIONS

"Bond." Merriam-Webster, Merriam-Webster, www.merriam-webster.com/dictionary/bond.*
(Continued)

*Primary Examiner* — Justin C Mikowski
*Assistant Examiner* — Madison Emanski
(74) *Attorney, Agent, or Firm* — Inskeep IP Group, Inc.

(57) ABSTRACT

X-ray procedure tables with improved structural strength that enable radiation shielding and integrated medical device and monitoring systems. The design allows the incorporation of an integrated patient support structure, radiation shielding and associated devices and conduits for medical care in procedures that employ X-ray imaging. The X-ray procedure table may be formed from a sled table attachable to a pedestal, with at least one side member extending along a bottom of the sled table to add structural rigidity.

13 Claims, 6 Drawing Sheets

Related U.S. Application Data

(60) Provisional application No. 62/734,190, filed on Sep. 20, 2018.

(58) Field of Classification Search
CPC .. A61B 6/0442; A61B 6/107; A61G 2203/80; A61G 2210/50
USPC .......................................................... 5/601
See application file for complete search history.

(56) References Cited

U.S. PATENT DOCUMENTS

| | | | |
|---|---|---|---|
| 4,893,323 A | 1/1990 | Cook, III | |
| 6,212,713 B1 | 4/2001 | Kuck et al. | |
| 6,769,145 B1* | 8/2004 | Pfeuffer | A61B 6/0442 |
| | | | 5/601 |
| 6,955,464 B1 | 10/2005 | Tybinkowski et al. | |
| 9,693,921 B2* | 7/2017 | Koger | A61G 7/1034 |
| 2002/0109107 A1* | 8/2002 | Goldstein | A61B 6/4423 |
| | | | 250/505.1 |
| 2004/0232916 A1 | 11/2004 | Kamimura et al. | |
| 2013/0205503 A1 | 8/2013 | Rozewicz et al. | |
| 2016/0158082 A1* | 6/2016 | Gainor | A61G 7/0524 |
| | | | 5/690 |
| 2017/0020466 A1 | 1/2017 | Moulin et al. | |
| 2017/0119324 A1* | 5/2017 | Wilson | G21F 3/00 |
| 2017/0332984 A1 | 11/2017 | Brendel et al. | |
| 2018/0008211 A1 | 1/2018 | Shang | |
| 2018/0221229 A1 | 8/2018 | Kaiser et al. | |

FOREIGN PATENT DOCUMENTS

| | | |
|---|---|---|
| JP | S49-046881 A | 5/1974 |
| JP | S61-023987 A | 2/1986 |
| JP | S61-058641 A | 3/1986 |
| JP | 2006-320637 A | 11/2006 |
| JP | 2008-228755 A | 10/2008 |
| JP | 2011-087988 A | 5/2011 |
| JP | 2014-069043 A | 4/2014 |
| WO | WO2016/090384 A2 | 6/2016 |
| WO | WO2016/090384 A3 | 6/2016 |

OTHER PUBLICATIONS

"Integral." Merriam-Webster, Merriam-Webster, www.merriam-webster.com/dictionary/integral.*
WIPO, U.S. International Search Authority, International Search Report and Written Opinion dated Dec. 11, 2019 in International Patent Application No. PCT/US2019/052280, 11 pages.
Japanese Patent Office, Office Action dated Mar. 14, 2023 with English translation in Japanese Patent Application No. 2021-515462, 11 pages.

* cited by examiner

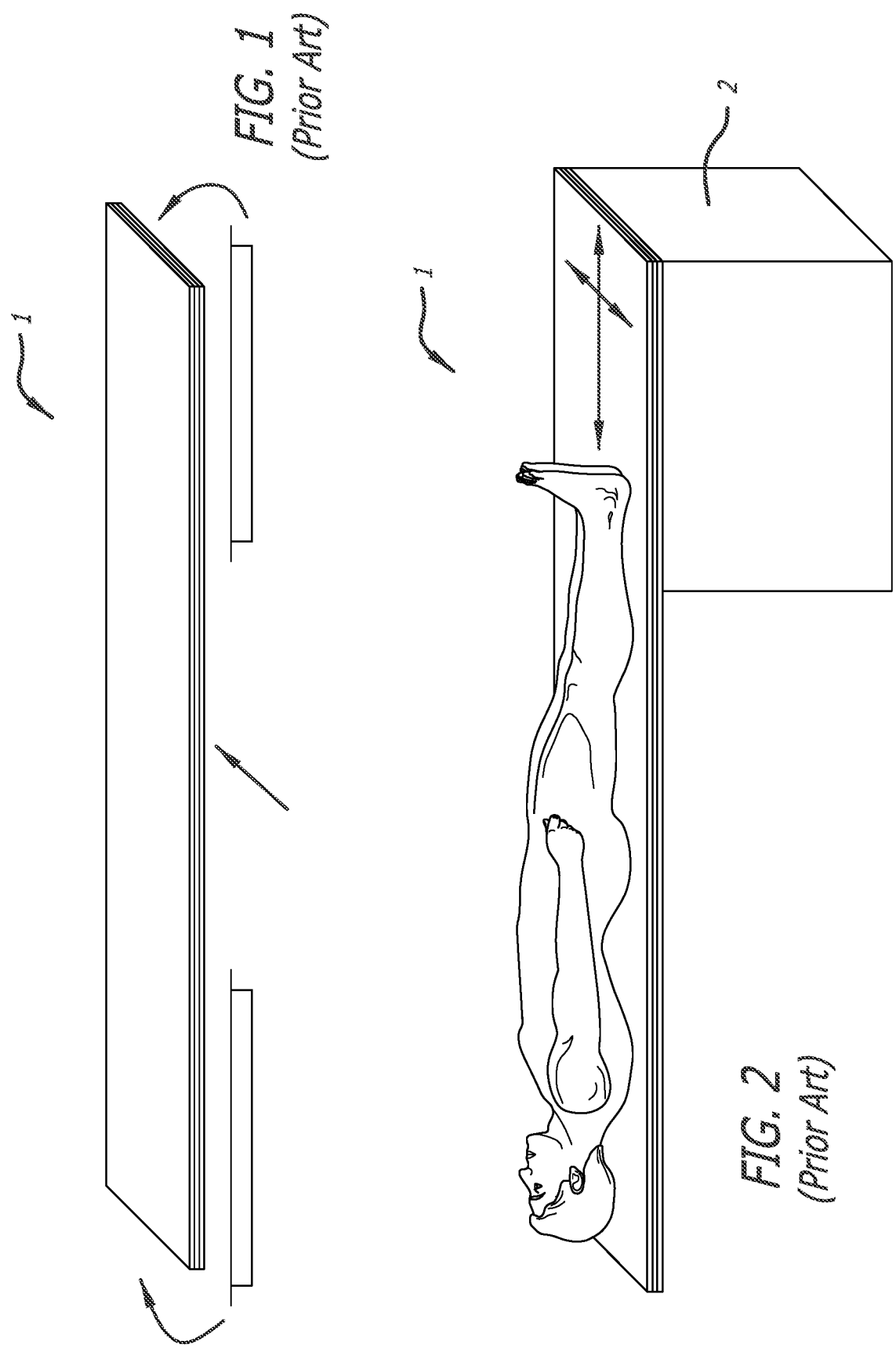

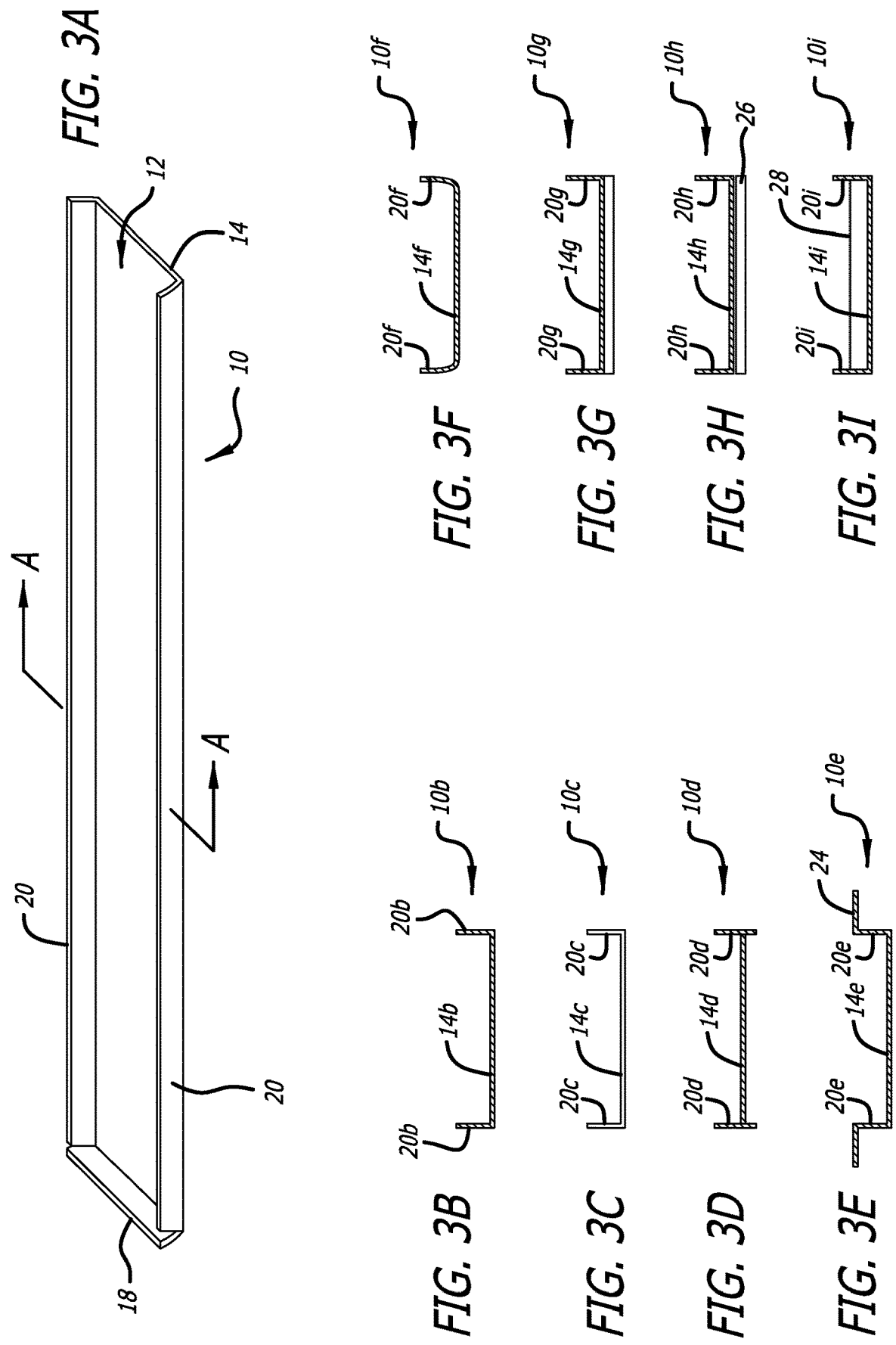

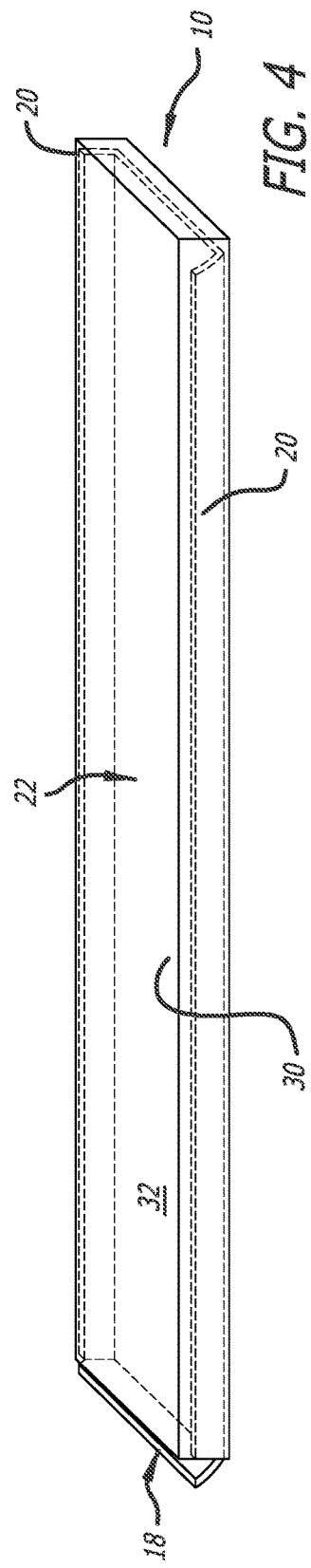
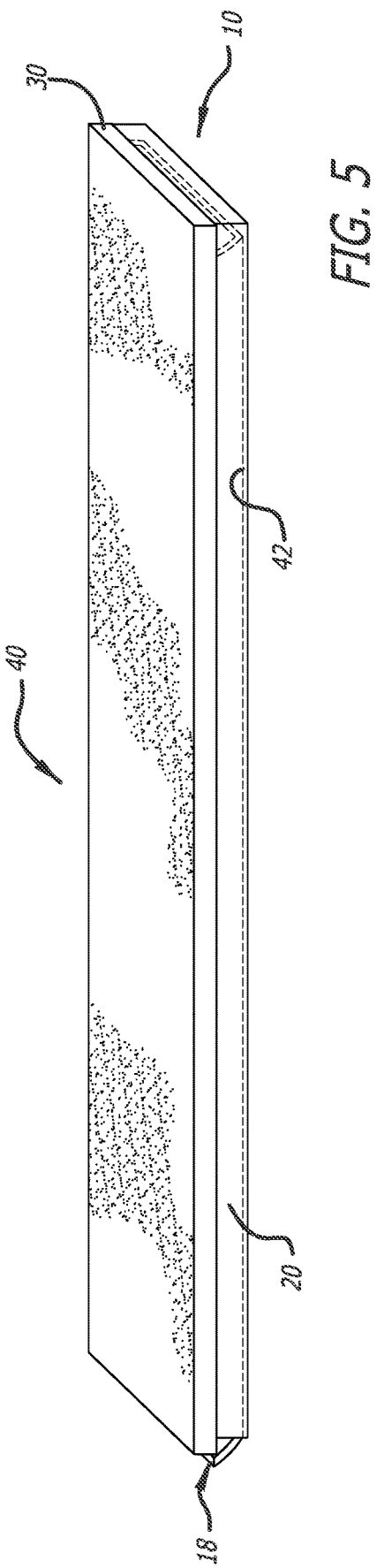

SLED-TABLE FOR RADIOGRAPHIC IMAGING AND MEDICAL DEVICE INTEGRATION

RELATED APPLICATIONS

This application is a continuation of and claims priority to U.S. patent application Ser. No. 16/578,128 filed Sep. 20, 2019 entitled A Sled-Table For Radiographic Imaging And Medical Device Integration, which claims benefit of and priority of U.S. Provisional Application Ser. No. 62/734,190 filed Sep. 20, 2018 entitled A Sled-Table For Radiographic Imaging And Medical Device Integration, both of which are hereby incorporated by reference in their entireties.

BACKGROUND OF THE INVENTION

When undergoing medical procedures that employ radiologic imaging of the body, patients typically lie on a radiolucent X-ray table 1 (FIGS. 1 and 2). The tables are often constructed from a carbon fiber and are shaped like a thin beam. The beam extends out from a pedestal 2 that is fixed to the floor or ceiling. A patient lies on a foam mat that sits independently atop the table top. The pedestal often contains a motorized system for adjusting the table height and pitch relative to the procedure room floor. Typically, the carbon fiber beams extend asymmetrically from the pedestal, like a diving board.

The diving board like configuration forms a lever, where the weight of the patient at the end of the diving board creates significant stress on the table. When excessive weight is applied, the table can bend, or structurally fail and break, leading to injury or death. Importantly, the table is not just exposed to the weight of the patient, but it also carried the load of any attached component and the loads applied during procedures such as cardiopulmonary resuscitation. As a result, weight limits have been placed on X-ray tables and these weight limits restrict the addition of other devices to the table. As a consequence, X-ray rooms have a number of devices on floor mounts positioned near the table with cables draping into the sterile field of the procedure. This creates safety and infection hazards, and often slow down workflow and movement in the procedure room as the floor-mounted devices do not move in unison with the movement of the table.

Another problem in X-ray laboratories is exposure of the staff to scatter radiation from the patient. X-ray emanating from the X-ray tube housing leak or reflected from the patient and leads to staff radiation exposure. This exposure has been identified as a significant health risk. Radiation shielding for such procedures has been limited because shielding is heavy. The structural limits of the X-ray table and the lack of attachment points beyond the mid-point of the table have led to an inability to attach significant shielding to the X-ray table, particularly around the mid and head of the table, where scatter radiation is the greatest.

Patients undergoing X-ray procedures also often need monitoring of their vital signs, such as blood pressure, electrocardiogram, respiration, and blood oxygen concentration. In addition, many devices other than X-ray imaging are often employed during these procedures. For example, ultrasound imaging is often used for vascular access and biopsies. Intravascular ultrasound is used to image blood vessels during procedures. Intravascular pressure measurement catheters are attached to electronic devices outside the body. Infusion pumps are used to infuse fluids, such as saline or X-ray contrast media. Therapeutic tools such as atherectomy devices are used as well. In addition, during procedures patients often require medical gasses such as oxygen, nitrous oxide, air, nitric oxide or other agents. In some cases, suction might be needed to aspirate body fluids.

Typical X-ray tables cannot handle these additional needs because they have no internal chambers and their structural design imposes significant weight limits due to limited structural beam strength.

OBJECTS AND SUMMARY OF THE INVENTION

The present invention addresses the aforementioned shortcomings and limitations of prior art X-ray tables but providing structurally stronger table designs without adding limitations to the functionality of the tables. The present invention also provides devices for retrofitting existing tables to make them stronger.

One aspect of the invention provides an X-ray table having a pedestal and a sled table, the sled table including a bottom attached to the pedestal and having a first end and a second end, the second end attached to the pedestal and the first end extending from the pedestal such that only the second end is supported by the pedestal; and side members extending along the bottom between the first end and the second end and adding structural rigidity to the sled table.

The bottom and the side members may have upper edges and lower edges, the lower edges attached to the bottom such that the side members extend upwardly from the bottom.

The bottom and the side members may have double-wall construction.

The bottom and the side members may have upper edges and lower edges and the side members may be attached to the bottom between the upper and lower edges to form an I-beam construction with the bottom. The I-beam construction may in some embodiments, form a first cavity above the bottom and between the side members and a second cavity below the bottom and between the side members, and wherein the upper cavity is larger than the lower cavity.

One aspect of the invention provides a mattress received by the upper cavity.

Another aspect provides side members have upper edges and further comprising arm rests extending outwardly from the upper edges of the side members.

Yet another aspect of the invention includes side members that are curved and extend upwardly from the bottom.

The bottom may be a beam structure.

In one aspect a separate beam is included and the bottom is bonded to a top of the beam.

The table may include a cross member extending between the sidewalls and spaced apart from the bottom to form a cavity between the cross member, the bottom and the side members.

Another aspect of the invention is a method of improving the strength and rigidity of an existing X-ray table having a table top and a pedestal comprising attaching side members along longitudinal sides of the table top.

In one aspect of the method, the side members have brackets that receive the longitudinal sides of the table top.

Attaching the side members along the longitudinal sides of the table top may involve bonding the table top to the brackets.

In at least one embodiment of the method, the side members are attached to each other with upper and lower cross-members to form a sleeve and the side members are attached to the table top by sliding the sleeve over the table top.

Yet another aspect of the invention provides a sled table attachable to a pedestal for forming an X-ray table. The sled table includes a bottom attached to the pedestal and having a first end and a second end, the second end attached to the pedestal and the first end extending from the pedestal such that only the second end is supported by the pedestal; side members extending along the bottom between the first end and the second end and adding structural rigidity to the sled table; a foam mattress resting within a cavity formed between the sidemembers and above the bottom; and a cover spanning the foam mattress and sealed to the side members, the cover including an impermeable top surface.

The cover may be a pad.

The sled table may have rails extending along the side members and defining a cavity through which wires and gas lines may be contained.

The sled table may also include a compartment within the cavity containing an electronic controller fed by the wires and/or gas lines.

The compartment may have vent holes allowing heat to escape the compartment.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 1 is a perspective view of a prior art table top;

FIG. 2 is a perspective view of a prior art table;

FIG. 3A is a perspective view of an embodiment of the invention;

FIG. 3B is a cross-section of an alternative embodiment to FIG. 3A as if taken along section lines A-A of FIG. 3A;

FIG. 3C is a cross-section of an alternative embodiment to FIG. 3A as if taken along section lines A-A of FIG. 3A;

FIG. 3D is a cross-section of an alternative embodiment to FIG. 3A as if taken along section lines A-A of FIG. 3A;

FIG. 3E is a cross-section of an alternative embodiment to FIG. 3A as if taken along section lines A-A of FIG. 3A;

FIG. 3F is a cross-section of an alternative embodiment to FIG. 3A as if taken along section lines A-A of FIG. 3A;

FIG. 3G is a cross-section of an alternative embodiment to FIG. 3A as if taken along section lines A-A of FIG. 3A;

FIG. 3H is a cross-section of an alternative embodiment to FIG. 3A as if taken along section lines A-A of FIG. 3A;

FIG. 3I is a cross-section of an alternative embodiment to FIG. 3A as if taken along section lines A-A of FIG. 3A;

FIG. 4 is a perspective view of an embodiment of the invention;

FIG. 5 is a perspective view of an embodiment of the invention;

DESCRIPTION OF EMBODIMENTS

Figure 6:
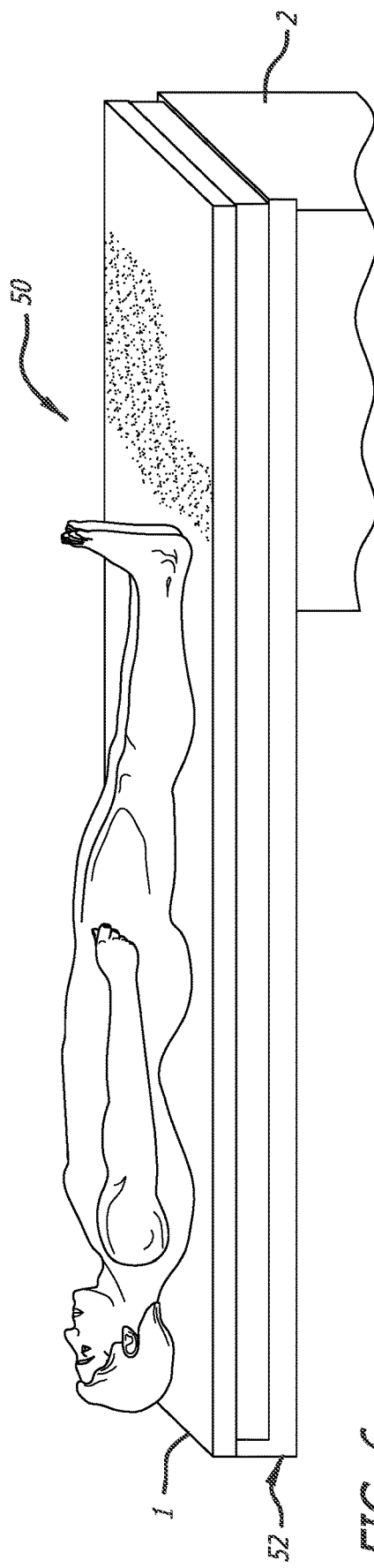
FIG. 6 is a perspective view of an embodiment of the invention.

Specific embodiments of the invention will now be described with reference to the accompanying drawings.

This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The Sled-Table

Referring now to the figures and first to FIGS. 3A-3I, there is shown an embodiment 10 of the table of the invention. Sled-table 10 is designed for X-ray imaging procedures where the table top 12 that is attached to a standard pedestal is in the form of an open sled having a bottom 14, a head wall 18 and sidewalls or side members 20 with upper and lower edges. The addition of the open side members 20 to the sled-table increases the rigid strength of the sled-table 10 and allow a greater weight limit. These side members 20 also greatly increase the torsional strength of the table, a critical factor when the table is loaded unevenly (e.g. during patient loading/unloading and often during emergency procedures such as manual chest compressions).

The construction of the sled-table 10 can take on many forms and still achieve the structural goals of the invention. For example, FIGS. 3B-3I show various embodiments of cross sections of the sled-table 10. FIG. 3B shows an embodiment 10b in which a bottom 14b and and side members 20b are all single-wall construction.

FIG. 3C shows an embodiment 10c in which a bottom 14c and and side members 20c are all double-wall construction.

FIG. 3D shows an embodiment 10d in which a bottom 14d and and side members 20d form an I-beam as the side members 20d extend below the bottom 14d.

FIG. 3E shows an embodiment 10e that includes arm rests 24 extending outwardly from the top of the side members 20e. These arm rests 24 add further structural rigidity as the horizontal surfaces along the top surface of the structure are very resistant to beam bending.

FIG. 3F shows an embodiment 10f in which the side members 20f are slightly curved and flare outwardly from the bottom 14f.

FIG. 3G shows an embodiment 10g wherein the bottom 14g is a beam structure.

FIG. 3H shows an embodiment 10h having a bottom 14b and and side members 20b and the bottom 14b is bonded to the top of a beam 26.

FIG. 3I shows an embodiment 10i having a bottom 14i and and side members 20i and further includes a cross member 28 extending between the side members 20i and spaced above the bottom 14i. The placement of a second carbon fiber layer to the construct above the neutral axis of bending of the sled-table provides two benefits—the increased spacing of the horizontal beam from the bottom of the sled greatly improves the bending strength of the system. Additionally, the space between the bottom two layers of the sled may be used to contain wiring or other components that are isolated from the weight of the patient.

As shown in FIG. 4, a cavity 22 is created by the sides 20 and can be filled with a foam mattress 30 or other compressible material to form a surface 32 that is comfortable for the patient to lie on.

As shown in FIG. 5, the top of the sled 10 and mattress 30 can be reversibly sealed by a molded foam top 40 that contains a circumferential channel 42 that mates with the free edges of the sled top (head wall 18 and side walls 20). This reversible seal can be made relatively impermeable, reducing the risk of infectious contamination, while allowing for re-access to the inside of the sled-table to remove, add, or repair inner components.

Figure 7:
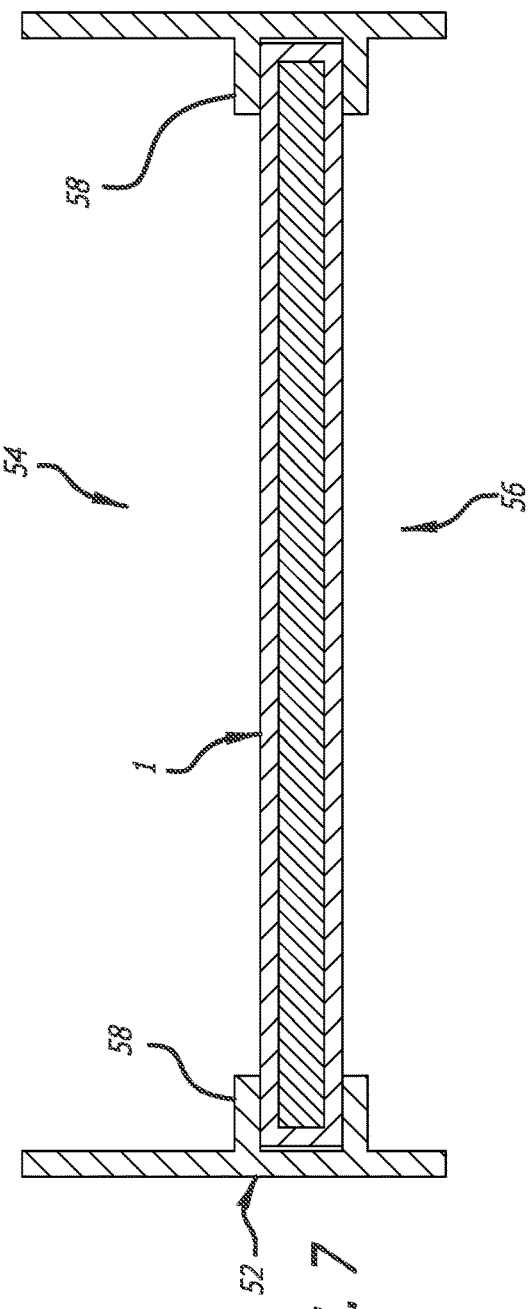
FIG. 7 is an elevation of an embodiment of the invention.
Figure 8:
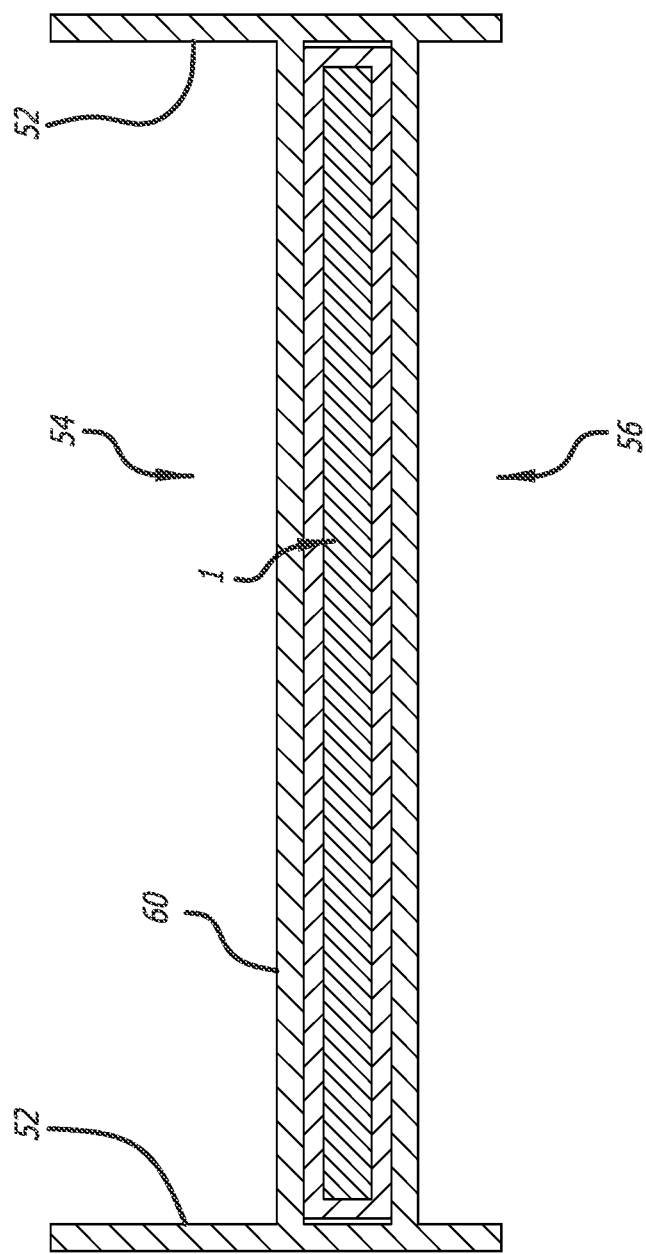
FIG. 8 is an elevation of an embodiment of the invention.

In an additional embodiment 50, shown in FIGS. 6-8, the I-beam feature 52 of the sled table is used to convert an existing table 1 to a sled table 50. This I-beam configuration increases the strength and rigidity of the table, allowing a higher weight load, particularly at the end opposite the pedestal 2. In FIG. 7-8 there are shown two methods of attachment. In the embodiment of FIG. 7, an I-beam 52 is bonded within brackets 58 to both table sides. This creates a first cavity 54 above the existing table 1 and a second cavity 56 below the existing table 1. The I-beam is best configured as an asymmetric I-beam because the cavity 54 above the table is bigger, allowing for the placement of foam for patient comfort.

In the embodiment of FIG. 7, the I-beams 52 have brackets 58 for receiving the existing table and creating a bonding and support surface. Alternatively, as seen in FIG. 8, the I-beam attachment to the existing table can be in the form of a sleeve 60 that fits over the existing table 1. This configuration provides additional strength due to the inner beam surrounding the existing table top.

The key to improving the stiffness of the table is to increase the cross-sectional moment of inertia (I) of the table. The greatest gains in the cross-sectional moment of inertia are accomplished by placing material at a distance from the bending plane of the construct. For a standard table with a generally rectangular cross section, these gains are achieved by making the table thicker—the upper and lower surfaces of the table are the greatest distance from the bending plane, also known as the neutral axis, which is the centerline of the height of the table. An improved moment of inertia for a rectangular cross-section can be achieved by making the table thicker. However, a carbon fiber table with too great of a thickness affects how close the beam can get to the patient, impacting the X-ray image quality. In this invention, because the structural sled-table incorporates the height of the mattress, the overall height of the structural component is significantly greater than that of the standard table, thus increasing the cross-sectional moment of inertia and the overall stiffness of the system. As an example, a hypothetical rectangular table with 0.150" wall thickness, 2" in height and 18" in width has a cross-sectional moment of inertia of 4.75 in$^4$. A simple I-beam design turned on it's side such as that shown in FIG. 3D with a flange height of 3" both above and below the table, a 0.150" wall thickness and 18" in width has a cross-sectional moment of inertia of 5.40 in$^4$, a 13.6% increase in moment of inertia that directly correlates to weight capacity in bending under cantilever load in this application. More complex cross sections as shown in 3E and 3G-3I have even larger cross-sectional moments of inertia which will translate to even better system performance under load and increased cath lab table weight capacity.

The presence of a side to the sled-table allows attachment of rails and radiation shielding. In an additional embodiment, radiation shielding material can be attached to the sides of the sled, including to the arm boards, which can have a vertical edge that allows easy attachment of shielding. In an additional embodiment, a one or more rail systems can be attached to the sled sides. The rail system can be closed or hollow. A hollow rail can be used to carry medical gasses, electrical power, electronic data wiring, or other conduits in order to isolate them from the sterile field. In one embodiment, disposable conduit material can be attached to the rail and extend to the sterile field. In addition, automated cardio-pulmonary resuscitation devices can be attached to the rails, increasing the speed and stability of attachment around the patient.

A closed rail can be attached to the vertical surface of the sled-table and radiation shielding can be attached to the rail. A circular rail allows the radiation shielding material to swing on the rail. This is advantageous for C-arm X-ray systems where the X-ray gantry can push the shielding away by causing it to swing outwardly on the rail.

In another embodiment, the horizontal (bottom) portion of the sled can contain conduit material. The conduits can be in the form of an I-beam, such that one portion is closed by the horizontal surface and the opposite portion is open. It is recognized that the conduits could take many different embodiments, based on the size required, the desire for additional rigid strength, and radio-opacity.

The Sled-Table Cavity—Sealing Problems and Solution

The existence of a cavity produced by the sled-table configuration creates the opportunity to fill the cavity with foam to improve patient comfort while lying on the sled-table during a procedure (FIG. 4). One problem with foam inserts is that blood or other body fluids can ingress into the foam or the inner cavity of the sled-table. One solution would be to wrap the table in an impermeable material (such as a coated vinyl cloth or polymer sheet material). The disadvantage is that such a wrap prevents reentry into the sled-table cavity without damaging the covering. The problem with an alternative of having a covering with a reversible seal, such as a zipper or hook-and-eye type sealing, is that the seals can often be breached and the sealer itself have crevices that are difficult to clean.

In the invention described here, the top of the sled-table can be sealed with a pad having an impermeable surface (FIG. 5). The pad has a channel around the perimeter. The channel mirrors the edge of the sled-table side rim and is of a width such that the channel fits tightly onto the channel (FIG. 5). It is anticipated that an elastomeric foam material may be used, and the dimension of the foam channel would be adjusted to provide a friction fit sufficient to prevent fluid entry through the sealing edge.

There are a number of additional embodiments for the sealing pad. The foam pad can be wrapped in an impermeable cloth or like material, where the cloth provides a surface to the foam. The cloth material can be bonded to all or part of the foam pad. The channel in the sealing pad can be composed of a U-channel (or other shape) that is set or molded into the sealing pad. The foam itself can be a blend of different types of foam and different elasticities. The sealing pad can also be constructed without the use of foam. Alternative polymers or simply an impermeable cloth bonded or otherwise attached to a sealing channel can be used.

Rails and Electronic Components within the Sled-Table

Figure 9:
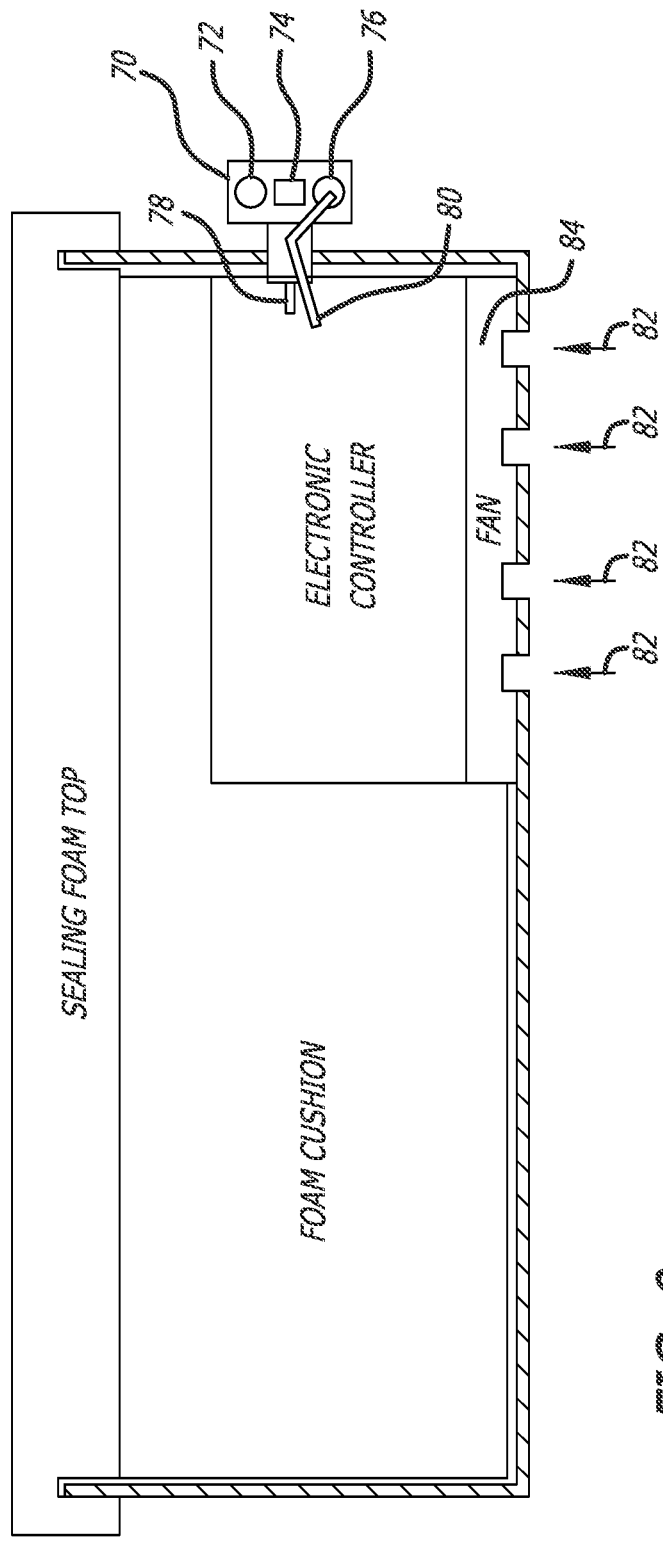
FIG. 9 is an elevation of an embodiment of the invention.

Unlike existing table designs, the presence of vertical surfaces on the sled-table allows the addition of attached rails 70, as described above, as seen in FIG. 9. Hollow rails 70 can be used to carry conduits 72, 74, 76 and 78 for medical gasses, suction, electricity, and electronic data transmission, respectively. This reduces the need for wires, cables, and tubing to drape into the sterile field from devices or sources around the room, improving safety from accidental disconnection, reducing tripping hazard, and reducing infectious entry into the sterile field. It is anticipated that the sled-table would be attached to a source for medical gasses and suction at a single point (for each agent) at the end of the sled-table where the connection is not in the way of workflow in the room. Similarly, connection to other medical device networks and power sources are positioned in order to minimize impact on workflow.

The presence of rails with internal conductors on the vertical surfaces of the sled-table allow the connection of those conductors to the inner sled-table cavity. This allows the placement of electronic controllers 80, monitors, and other devices used to monitor, diagnose, and treat the patient into the sled-table. As a result, these devices do not need to be attached to the floor or ceiling mount. Attachments to the internal devices or medical gasses are situated on the rail or extending from the rail in most cases. Consequently, the cable length to the patient is minimized because the rails can extend the length of the sled-table due to the vertical surface of the sled-table.

The ability to re-enter the internal sled-table cavity also allows for servicing of the internal components with the ability to reseal the cavity. Vent holes 82 on the bottom of the sled-table permit ventilation of the cavity and the heat generated by the electronic components, with minimal risk of body fluid contamination. A fan 84 could further be included in the table to increase cooling.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A sled table attachable to a pedestal for forming an X-ray table, comprising:
   a bottom including a first end, a second end, an upper surface, and a lower surface, wherein the bottom is configured to be attached to the pedestal in a cantilever arrangement, and wherein that the lower surface faces toward the pedestal and the top surfaces faces away from the pedestal when the bottom is attached to the pedestal;
   at least one side member extending along the bottom between the first end and the second end so as to add structural rigidity to the sled table, the at least one side member being integral with the bottom; and,
   wherein the at least one side member extends upwardly beyond the upper suface of the bottom to form a first cavity, wherein the first cavity extends at least partially between the first end and the second end of the bottom.

2. The sled table of claim 1, wherein the at least one side member is comprised of a first slide member extending along a first side of the sled table and a second side member extending along a second side of the sled table.

3. The sled table of claim 1, further comprising a mattress positioned within the first cavity.

4. The sled table of claim 3, further comprising a cover spanning the mattress, wherein the cover includes an impermeable top surface.

5. The sled table of claim 4, wherein the cover is sealed to the at least one side member.

6. The sled table of claim 4, wherein the cover is comprised of a pad.

7. The sled table of claim 1, further comprising at least one rail extending along the at least one side member.

8. The sled table of claim 7, wherein the at least one rail defines a second cavity through which one or more wires or gas lines may extend.

9. The sled table of claim 8, further comprising an electronic controller positioned within the second cavity.

10. The sled table of claim 8, wherein the cavity is vented by at least one vent hole.

11. The sled table of claim 1, wherein the at least one side member is curved.

12. The sled table of claim 1, further comprising a beam and wherein the bottom is bonded to a top of the beam.

13. A sled table attachable to a pedestal for forming an X-ray table, comprising:
   a bottom including a first end, a second end, an upper surface, and a lower surface, wherein the bottom is configured to be attached to the pedestal in a cantilever arrangement such that the proximal end of the bottom is supported by the pedestal and the distal end of the bottom is not supported by the pedestal, wherein the lower surface faces toward the pedestal and the upper surface faces away from the pedestal when the bottom is attached to the pedestal; and wherein:
   a first side member extending upwardly from a first side of the bottom;
   a second side member extending upwardly from a second side of the bottom;
   wherein the first side member and the second side member each extend upwardly beyond the upper surface of the bottom; and
   a cavity defined between the first side member and the second side member.

* * * * *